(12) United States Patent
Fitzgerald et al.

(10) Patent No.: US 6,341,182 B1
(45) Date of Patent: Jan. 22, 2002

(54) METHOD AND APPARATUS FOR ANALYZING AN IMAGE

(75) Inventors: Stephen Peter Fitzgerald; Robert Ivan McConnell; John Victor Lamont, all of Co. Antrim (GB)

(73) Assignee: Randox Laboratories Ltd., Antrim (GB)

( * ) Notice: Subject to any disclaimer, the term of this patent is extended or adjusted under 35 U.S.C. 154(b) by 0 days.

(21) Appl. No.: 09/138,009

(22) Filed: Aug. 21, 1998

(30) Foreign Application Priority Data

Sep. 11, 1997 (EP) .............................................. 97307053

(51) Int. Cl.[7] .............................. G06T 7/00; G06T 5/30
(52) U.S. Cl. ........................ 382/273; 382/257; 382/205
(58) Field of Search ................................ 382/270, 273, 382/274, 275, 132, 133, 128, 129, 172, 173, 195, 205, 256, 257, 191, 254, 308; 702/22

(56) References Cited

U.S. PATENT DOCUMENTS

| | | | |
|---|---|---|---|
| 4,952,805 A | | 8/1990 | Tanaka |
| 5,133,020 A | * | 7/1992 | Giger et al. .................. 382/128 |
| 5,230,026 A | * | 7/1993 | Ohta et al. ................... 382/134 |
| 5,304,498 A | * | 4/1994 | Ekins .......................... 436/501 |
| 5,488,567 A | * | 1/1996 | Allen et al. .................... 702/26 |
| 5,717,778 A | * | 2/1998 | Chu et al. .................... 382/133 |

FOREIGN PATENT DOCUMENTS

EP  0 874 242 A1  10/1998

* cited by examiner

*Primary Examiner*—Scott Rogers
(74) *Attorney, Agent, or Firm*—Oliff & Berridge

(57) ABSTRACT

A method of analysing an image to obtain an image value. The image comprises a defined array of pixel values. The method comprises (1) determining the highest pixel value in the image;
(2) calculating a lower threshold pixel value from the highest pixel value determined in step (1) in accordance with a predetermined algorithm; and
(3) obtaining the image value by statistically analysing the pixel values in the image which lie in a range defined by the lower threshold pixel value calculated in step (2).

22 Claims, 13 Drawing Sheets

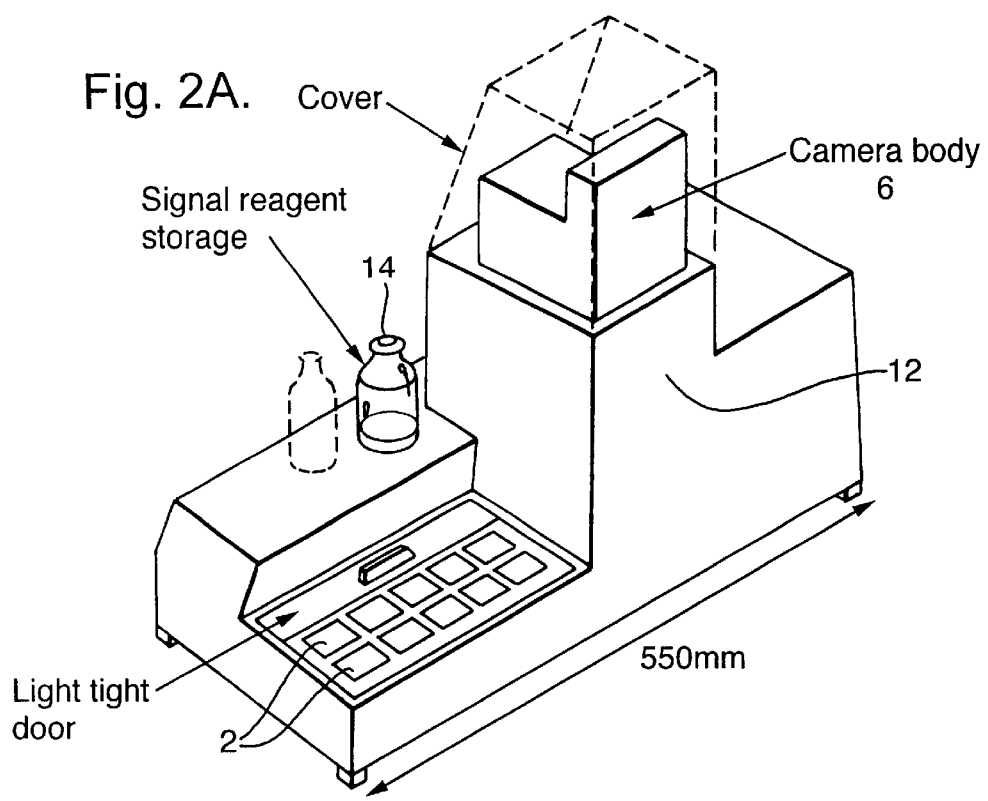
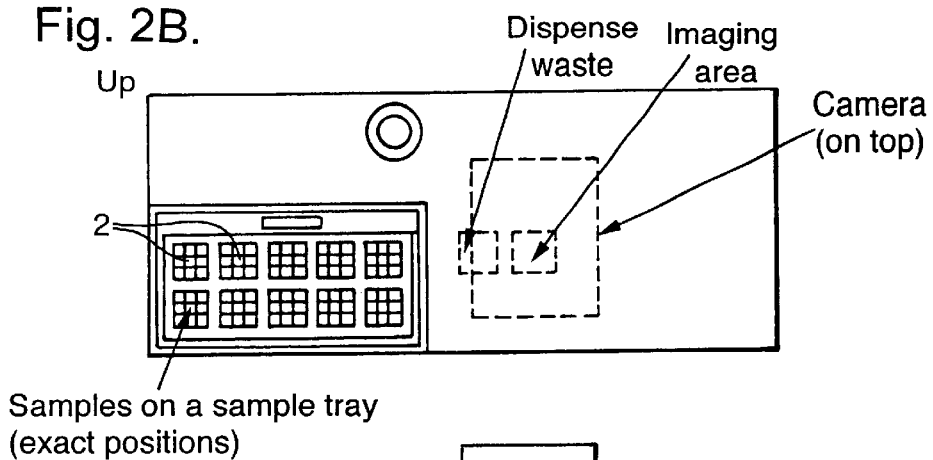
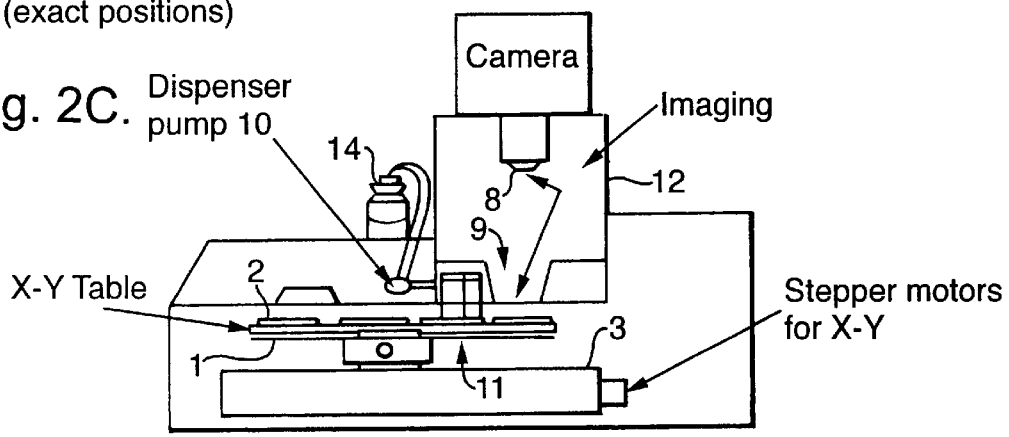

Spots 1-12 represent discrete

Sulphonamide antibody spots 1 cm² ceramic substrate

Fig.9.

eg. Consider a bright spot with a high background:

| 22 | 29 | 25 | 16 | 33 |
|----|----|----|----|----|
| 25 | 190 | 290 | 80 | 19 |
| 24 | 220 | 630 | 130 | 20 |
| 27 | 80 | 250 | 43 | 27 |
| 24 | 18 | 19 | 35 | 29 |

Raw Image

→ Erode →

| 22 | 22 | 16 | 16 | 16 |
|----|----|----|----|----|
| 22 | 22 | 16 | 16 | 16 |
| 24 | 24 | 43 | 19 | 19 |
| 18 | 18 | 18 | 19 | 20 |
| 18 | 18 | 18 | 19 | 27 |

Eroded Image

↓ Dilate

| 22 | 22 | 16 | 16 | 16 |
|----|----|----|----|----|
| 24 | 43 | 43 | 43 | 19 |
| 24 | 43 | 43 | 43 | 20 |
| 24 | 43 | 43 | 43 | 27 |
| 18 | 18 | 19 | 27 | 27 |

Opened Image

← Subtract From Raw

| 0 | 7 | 0 | 0 | 17 |
|---|---|---|---|----|
| 1 | 147 | 247 | 37 | 0 |
| 0 | 177 | 587 | 187 | 0 |
| 3 | 37 | 207 | 0 | 0 |
| 6 | 0 | 0 | 8 | 2 |

Subtracted Image
(SET TH=18 TO GET CLEAN SPOT)

This is 1 iteration. Increased iterations mantain high spot signal and give smoother edges.

Multianalyte Sulponamide Assay CT800 GOPS

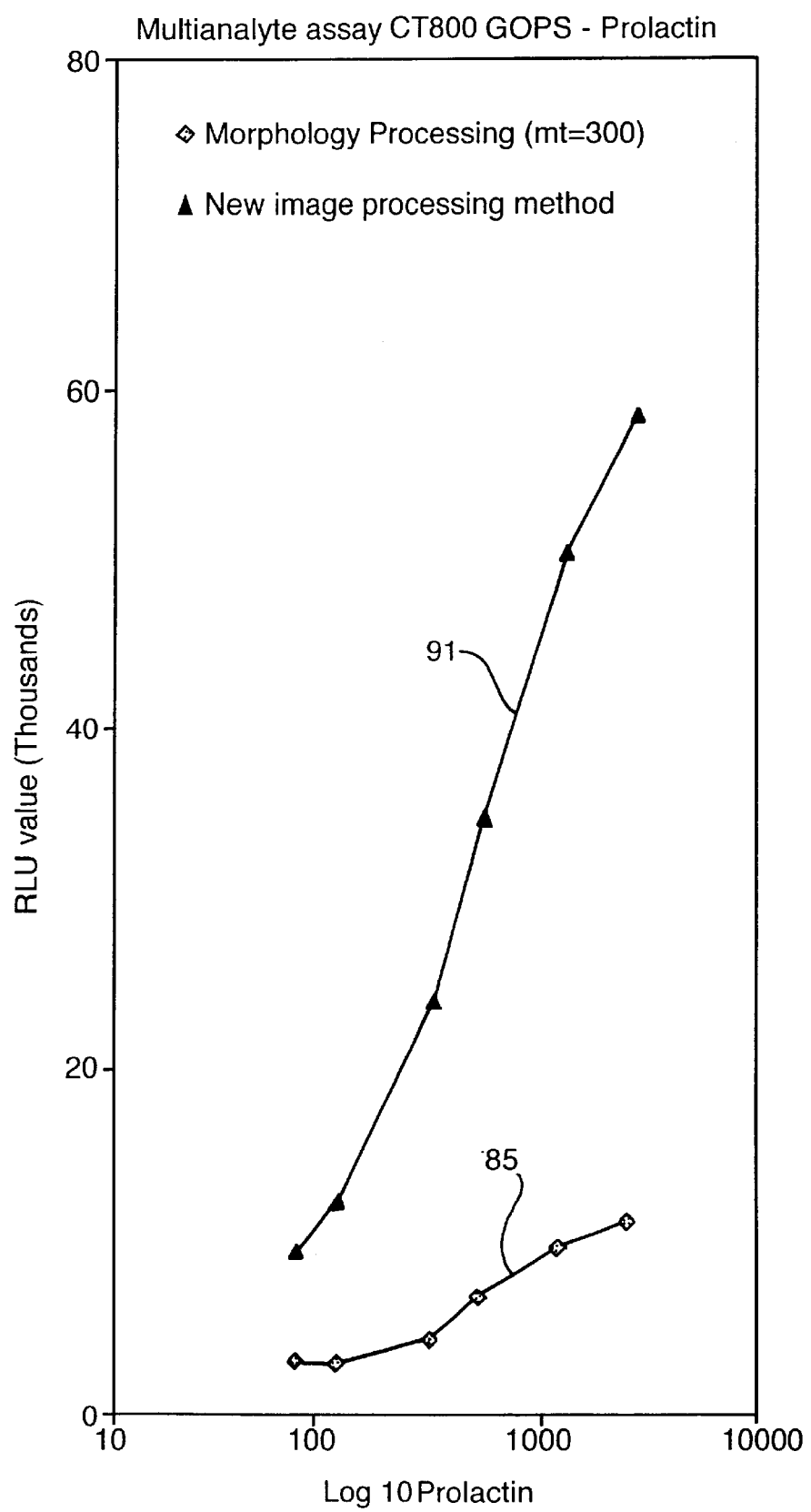

METHOD AND APPARATUS FOR ANALYZING AN IMAGE

FIELD OF THE INVENTION

The present invention relates to a method and apparatus for analysing an image.

DESCRIPTION OF THE PRIOR ART

A number of industrial applications require the analysis of an image of a localised feature. In particular, it may be desirable to analyze the image to determine the average brightness of the localised feature. However, the image of the localised feature may be more spread out than the original feature itself (for instance due to errors in the imaging process such as optical flare, or light from the original feature being reflected over adjacent areas). This causes the problem that the average brightness is calculated over an area greater than the actual area of the original localised feature, and as a result the calculated average brightness is erroneously low.

This problem has conventionally been addressed by reducing the number of pixels which are averaged. For instance, only pixels lying above a fixed lower threshold pixel value may be averaged. The disadvantage with this approach is that if the image of the localised area has low brightness, pixels which should be averaged may fall below the lower threshold pixel value. This results in a reduction in dynamic range and deviation from linearity in the average brightness measurement.

SUMMARY OF THE INVENTION

According to a first aspect of the present invention, there is provided a method of analysing an image to obtain an image value, the image comprising a defined array of pixel values, the method comprising (1) determining the highest pixel value in the image;
(2) calculating a lower threshold pixel value from the highest pixel value determined in step (1) in accordance with a predetermined algorithm; and
(3) obtaining the image value by statistically analysing the pixel values in the image which lie in a range defined by the lower threshold pixel value calculated in step (2).

The invention solves the problem outlined above by calculating the lower threshold pixel value from the highest pixel value. In contrast to the conventional approach which uses a fixed lower threshold pixel value, the invention uses a variable lower threshold pixel value which is related to the highest pixel value in the image. This results in increased linearity and increased dynamic range.

Any suitable statistical method may be employed in step (3), but preferably the image value is obtained in step (3) by averaging the pixel values. The average may be a median or mode average but preferably the average is a mean average. Alternatively, the statistical analysis may involve either summing or integrating the pixel values which lie within the defined range.

Typically, the pixel values are related to the intensity of radiation from an original image, and in a preferred embodiment the method further comprises detecting radiation from the original image to generate the array of pixel values. The total radiation intensity may be detected, or alternatively the intensity in one or more selected wavelength ranges may be detected.

A further problem can occur if the image contains erroneously high pixel values (eg. bright spots). This can result in the calculated image value being too high. This problem can be dealt with by calculating an upper pixel threshold value, and/or by removing high pixel values before the algorithm is performed, as discussed below.

Therefore, the method may further comprise calculating an upper pixel threshold value from the highest pixel value determined in step (1) in accordance with a second predetermined algorithm, wherein step (3) comprises statistically analysing the pixel values in the image which lie in a range defined by the upper and lower pixel threshold values. In some cases, the bright spots may be an order of magnitude higher than the image values in the rest of the image. Where the image is derived from an assay reaction site, this may be caused by cosmic rays. This will result in an erroneously large highest pixel value being used. Therefore, in this case, the method preferably comprises previously defining the defined array of pixel values by reviewing an original array of pixel values, and removing one or more of the highest pixel values in the original array of pixel values. This may be done automatically by statistical analysis, or by manual inspection. Both methods remove the bright spots from the averaging process and consequently improve accuracy.

The predetermined algorithm(s) may calculate the threshold(s) as any fixed function of the highest pixel value. For instance the thresholds may be calculated as the square root of the highest pixel value. Alternatively the highest pixel value may be input to a look-up table which has been previously loaded with a range of threshold values. However, preferably the lower and/or upper threshold pixel values are calculated as a predetermined percentage of the highest pixel value determined in step (1).

Typically, the lower threshold pixel value is between 50% and 90% of the highest pixel value determined in step (1), preferably substantially 80%.

Typically, the upper threshold pixel value is between 97% and 99% of the highest pixel value determined in step (1), preferably substantially 98%.

Background noise may be present in the pixel values resulting in a reduction in accuracy and dynamic range. Preferably, the background is removed from the pixel values, for instance by a method of mathematical morphology such as erosion, dilation, opening and/or thresholding. The background may be removed before or after step (1) or step (3).

In accordance with a second aspect of the present invention, there is provided a method of analysing an image to obtain a plurality of image values, the image comprising an array of pixel values, the method comprising dividing the image into a plurality of regions, and obtaining an image value from each region by a method according to the first aspect of the invention.

The second aspect of the present invention enables an image of a plurality of localised features to be analyzed.

Typically, the image is an image of a localised feature. For instance the localised feature may comprise a feature in a satellite image of the earth's surface, or a feature in a telescope image. However preferably the localised feature comprises a reaction site containing a reactive species which reacts with an analyte and which has been exposed to a test sample.

In accordance with a third aspect of the present invention, there is provided a method of analysing a localised reaction site containing a reactive species which reacts with an analyte and which has been exposed to a test sample, the method comprising detecting radiation from the reaction site to generate an image comprising an array of pixel values, the radiation being indicative of the presence or absence of the analyte in the test sample; and analysing the image by a method according to the first aspect of the invention, thereby obtaining an image value indicative of the presence or absence of the analyte in the test sample.

The third aspect of the present invention provides improved dynamic range and linearity in the analysis of an assay reaction site. Typically, the image value is an experimental parameter such as a relative light unit (RLU) value.

In accordance with a fourth aspect of the present invention, there is provided a method of analysing a plurality of localised reaction sites, each containing a reactive species which reacts with a respective analyte and each having been exposed to a test sample, the method comprising detecting radiation from the reaction sites to generate an image comprising an array of pixel values, the radiation from each reaction site being indicative of the presence or absence of a respective analyte in the test sample; dividing the image into a plurality of image regions each corresponding with a respective one of the reaction sites; and analysing each image region by a method according to the first aspect of the invention, thereby obtaining a plurality of image values each being indicative of the presence or absence of a respective analyte in the test sample.

The fourth aspect of the invention enables a multi-analyte assay to be processed quickly and efficiently.

Typically, the or each reaction site is located on a solid state substrate, and the or each reactive species comprises a ligand covalently bonded to the substrate.

Typically, the surface of the substrate between the reaction sites is inert with respect to analyte.

The image may be generated by illuminating the or each reaction site and detecting reflected or transmitted radiation. However, preferably the radiation comprises chemiluminescent, bioluminescent or fluorescent radiation emitted from the or each reaction site. In this case, a filter may be employed so as to only detect the narrow wavelength band of interest.

In accordance with a fifth aspect of the present invention, there is provided a method of performing an assay, the method comprising exposing one or more localised reaction sites to a test sample, each reaction site containing a reactive species which reacts with a respective analyte; and analysing the or each reaction site by a method according to the third or fourth aspects of the present invention.

According to a sixth aspect of the present invention, there is provided apparatus for analysing an image to obtain an image value, the image comprising a defined array of pixel values, the apparatus comprising (1) means for determining the highest pixel value in the image;
(2) means for calculating a lower threshold pixel value from the highest pixel value in accordance with a predetermined algorithm; and
(3) means for obtaining the image value by statistically analysing the pixel values in the image which lie in a range defined by the lower threshold pixel value.

According to a seventh aspect of the present invention, there is provided apparatus for analysing one or more reaction sites each containing a reactive species which reacts with an analyte and which has been exposed to a test sample, the apparatus comprising means for detecting radiation from the or each reaction site to generate an image comprising an array of pixel values; and means for analysing the image by a method according to the first or second aspect of the present invention, thereby obtaining one or more image values each being indicative of the presence or absence of a respective analyte in the test sample.

According to an eighth aspect of the present invention, there is provided apparatus for performing an assay, the apparatus comprising means for exposing one or more localised reaction sites to a test sample, each reaction site containing a reactive species which reacts with a respective analyte; and apparatus according to the seventh aspect of the present invention for analysing the or each reaction site.

BRIEF DESCRIPTION OF THE DRAWINGS

An example of a method and apparatus according to the present invention will now be described with reference to the accompanying drawings, in which:

FIG. 2 is a cross-section of an integrated analyzer system;

FIG. 9 illustrates opening;

FIGS. 11–16 are graphs of standard curves for FSH, LH and PL assays performed on silicon and ceramic substrates and image-processed using conventional techniques and using a method according to the present invention.

EMBODIMENT

Figure 1:
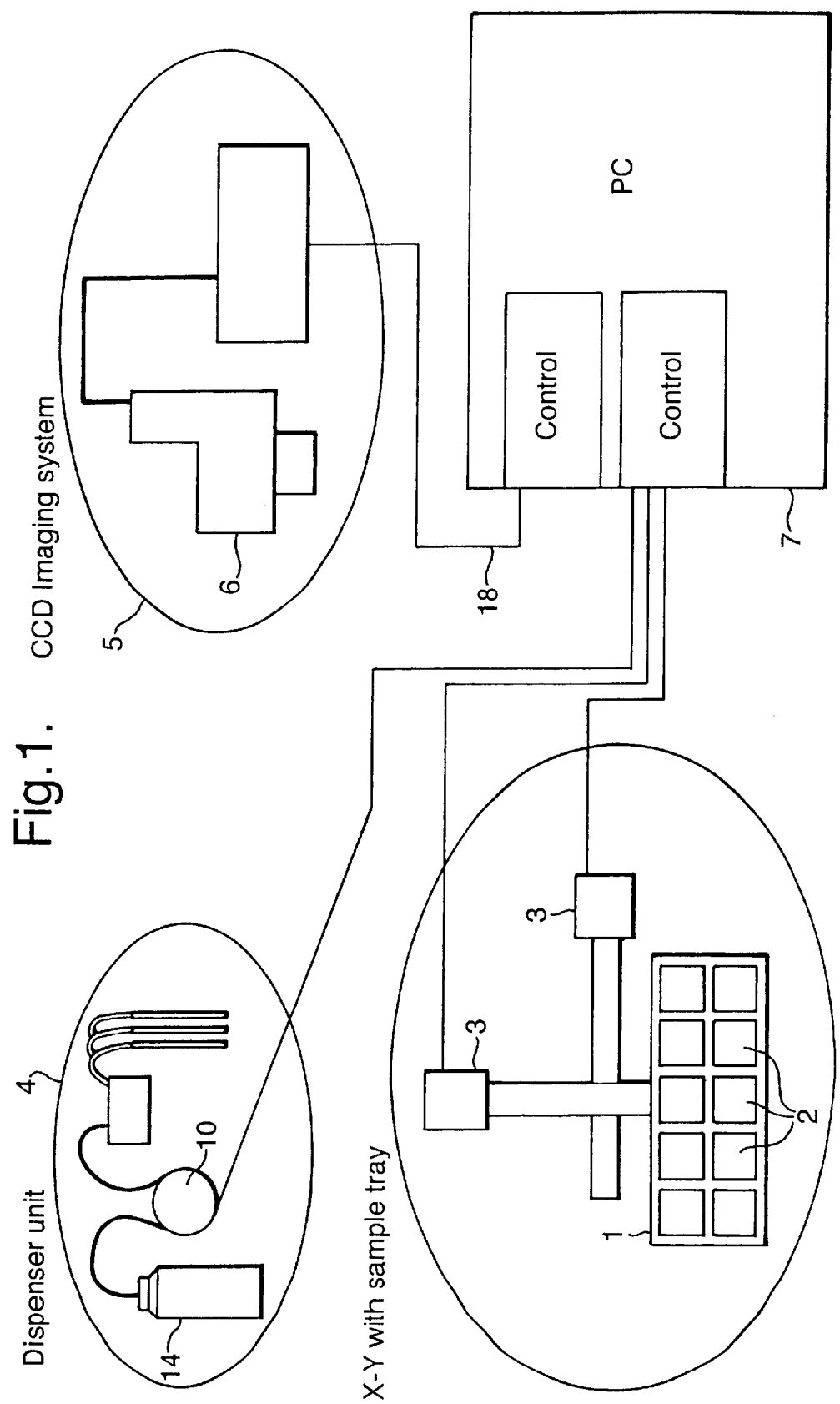
FIG. 1 is a schematic diagram of an integrated analyzer system.

FIG. 1 is a schematic diagram of an integrated analyzer system for the simultaneous, quantitative detection of a wide range of analytes in a multi-analyte format. The system may be used for clinical/veterinary diagnosis or drug screening. The system comprises a substrate platform 1 which carries an array of substrates 2. The platform 1 is controlled by X-Y translation controls 3 which position the platform at each stage of the analytical procedure. The translation controls 3 may be associated with a stepper motor (not shown) to achieve a positional accuracy of 10 micrometers. A dispenser unit 4 comprising fluid reservoir 14 and pump 10 dispenses fluids such as test samples, chemiluminescent reagent etc onto the substrates 2. A CCD imaging system 5 comprising a 2-dimensional CCD camera 6 images the substrates 2 to generate an image comprising an array of pixel values which are output on output line 18. The translation controls 3, dispenser unit 4, and CCD imaging system 5 are controlled by a conventional personal computer 7, which runs image processing software to process the images acquired by the CCD camera 6.

FIG. 2 illustrates a system of the type shown in the schematic diagram of FIG. 1. CCD camera 6 has a lens 8 which acquires an image of a substrate 2 in an imaging position 9. Liquids are dispensed with dispenser pump 10 onto a substrate 2 in a dispensing position 11. The lens 8 and imaging position 9 are enclosed in a dark box 12.

Figure 3:
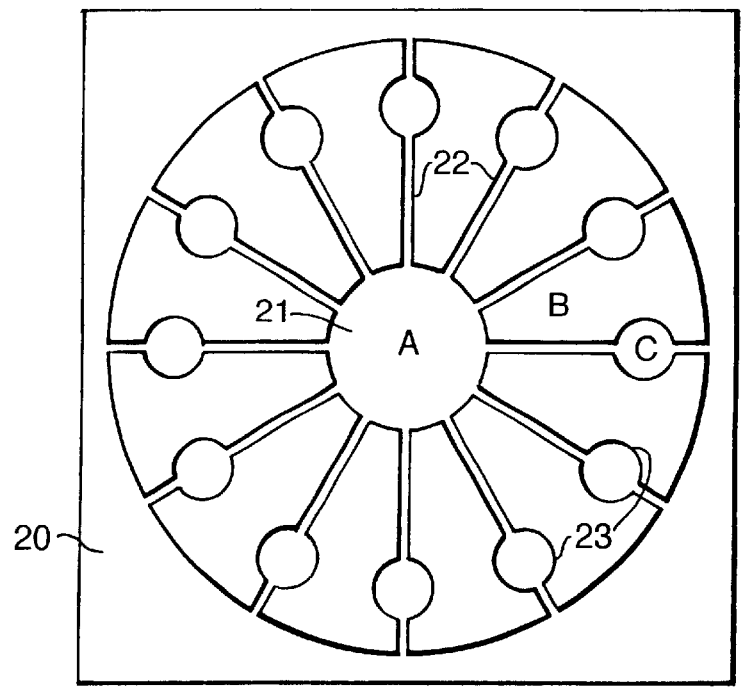
FIGS. 3–5 are examples of substrates for use in the analyzer system.
Figure 4:
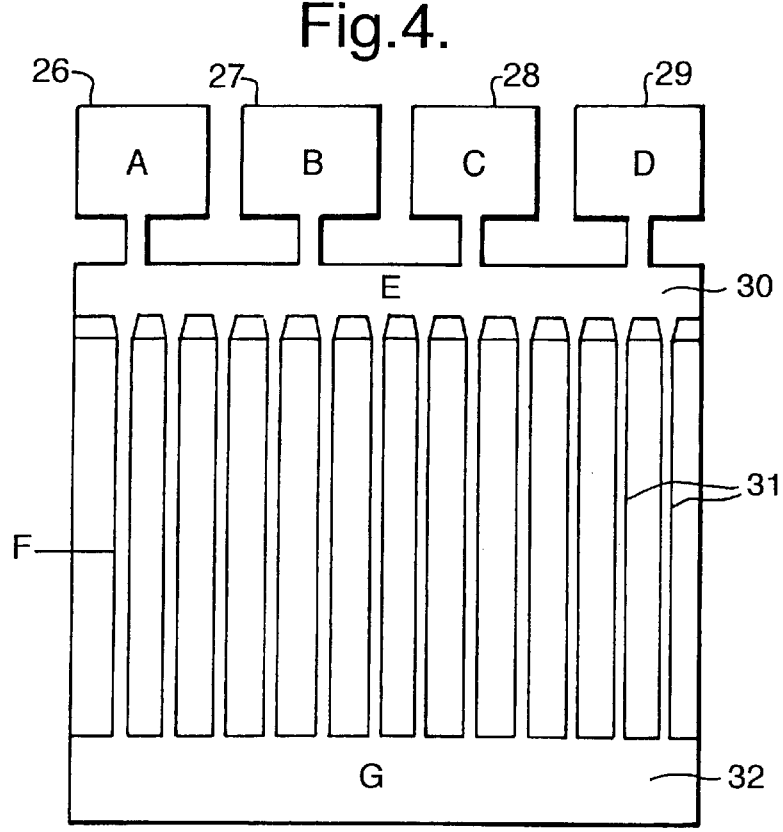
Figure 5:
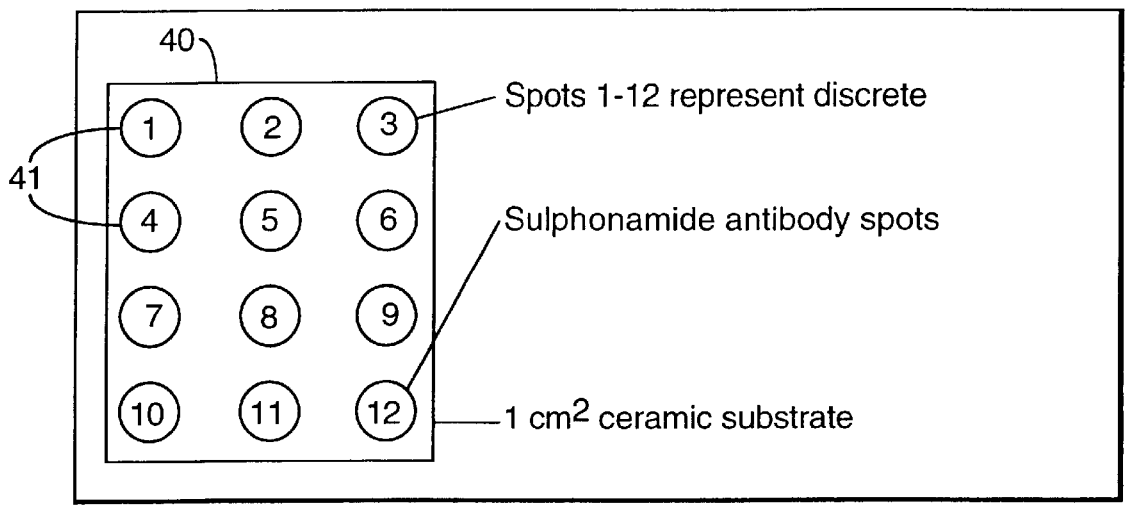

Substrates 2 of the form illustrated in FIGS. 3–5 are typically employed in the system of FIGS. 1 and 2. The substrates shown in FIGS. 3–5 are silicon or ceramic chips which have a plane surface which has been modified to incorporate a series of dimples/wells/pits, channels or chambers on the surface. These help to increase the surface area of the reaction sites, thereby providing the possibility of accelerating assay incubation time.

Referring to FIG. 3, a chip 20 has a central test sample reservoir 21 to which a liquid test sample is added when the chip 20 is at the dispensing position 11. Twelve channels 22 radiate from the reservoir 21 to respective reaction sites 23.

Referring to FIG. 4, chip 25 has four test sample reservoirs 26–29 to which liquid test sample is added at the dispensing position 11, a delivery manifold 30, test sample delivery channels 31 which deliver the test sample to reaction sites (not shown), and a waste reservoir 32.

Referring to FIG. 5, a chip 40 has twelve circular reaction sites 41. The chip 40 is a 1 cm$^2$ ceramic substrate.

Each reaction site 23,41 etc. bears a ligand covalently bonded to the substrate, and each ligand reacts with a respective different analyte. The ligands are immobilised in the spatially defined reaction sites by means of microfluidic dispensing of the ligand onto the substrate, which is chemically activated. The surface of the substrate between the reaction sites is inert with respect to the analyte. Suitable methods of preparing the reaction sites are described in more detail in co-pending European Patent Application No. 97302707.1. Covalent immobilisation of the biological ligand in the reaction site 23,41 etc is preferred since passive absorption interactions are susceptible to changes in pH, temperature and ionic strengths, and may in some instances result in release of weakly-bound ligands during incubation and washing steps, thus contributing to poor assay reproducibility.

Figure 6:
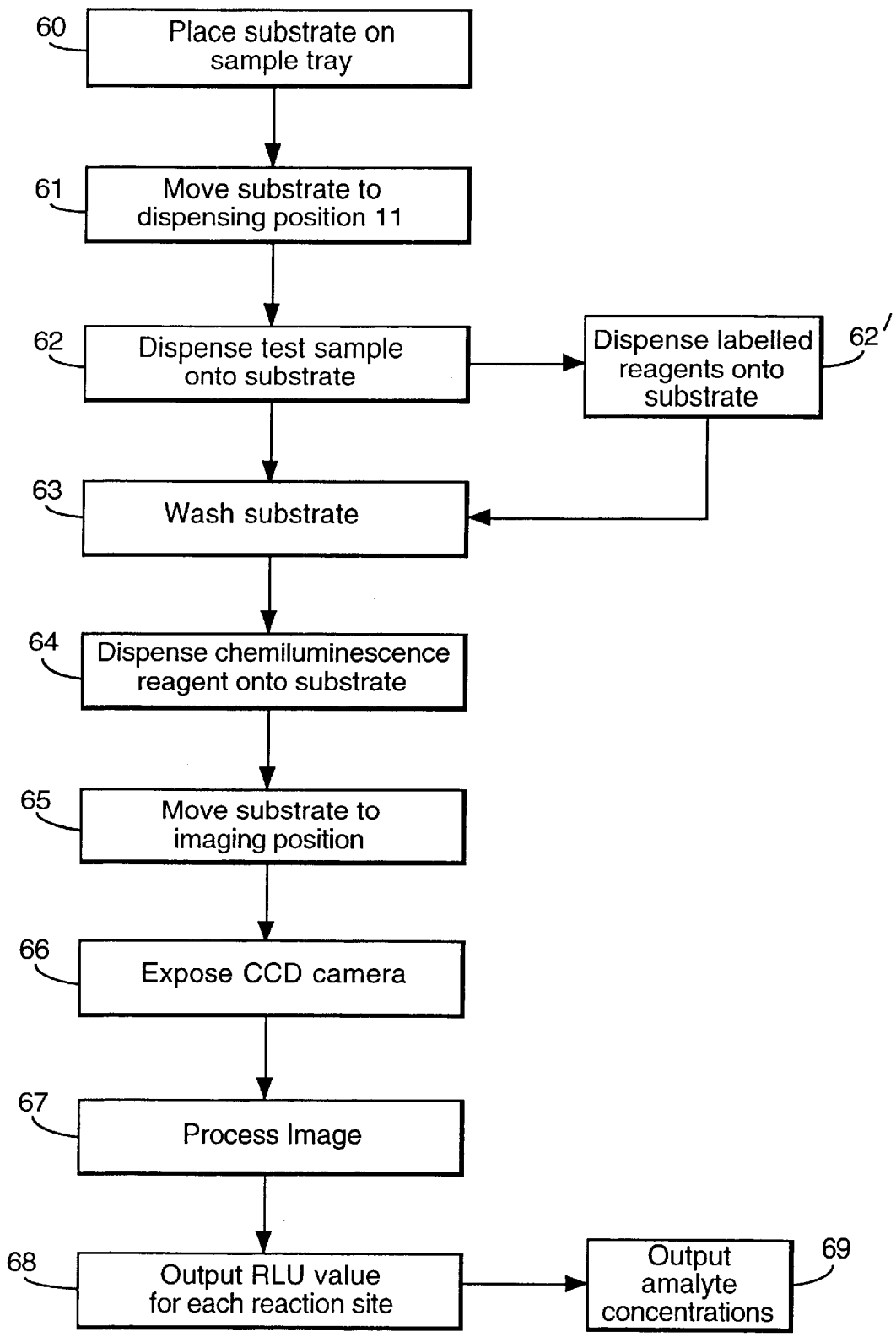
FIG. 6 is a flow diagram illustrating the main process steps in an assay.
Figure 10:
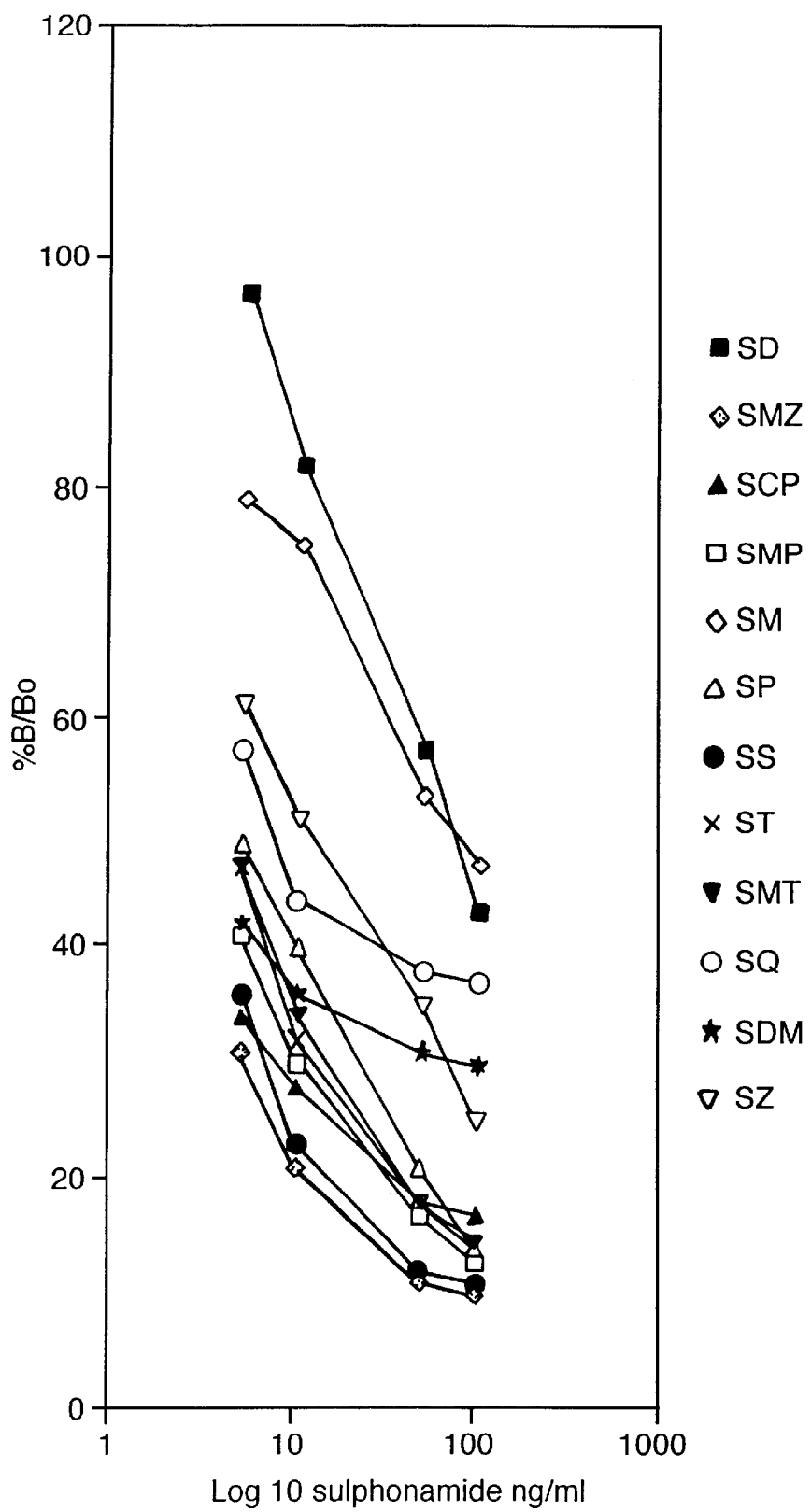
FIG. 10 is a graph of calibration curves for each of the 12 individual sulphonamides discussed in example 1.
Figure 11:
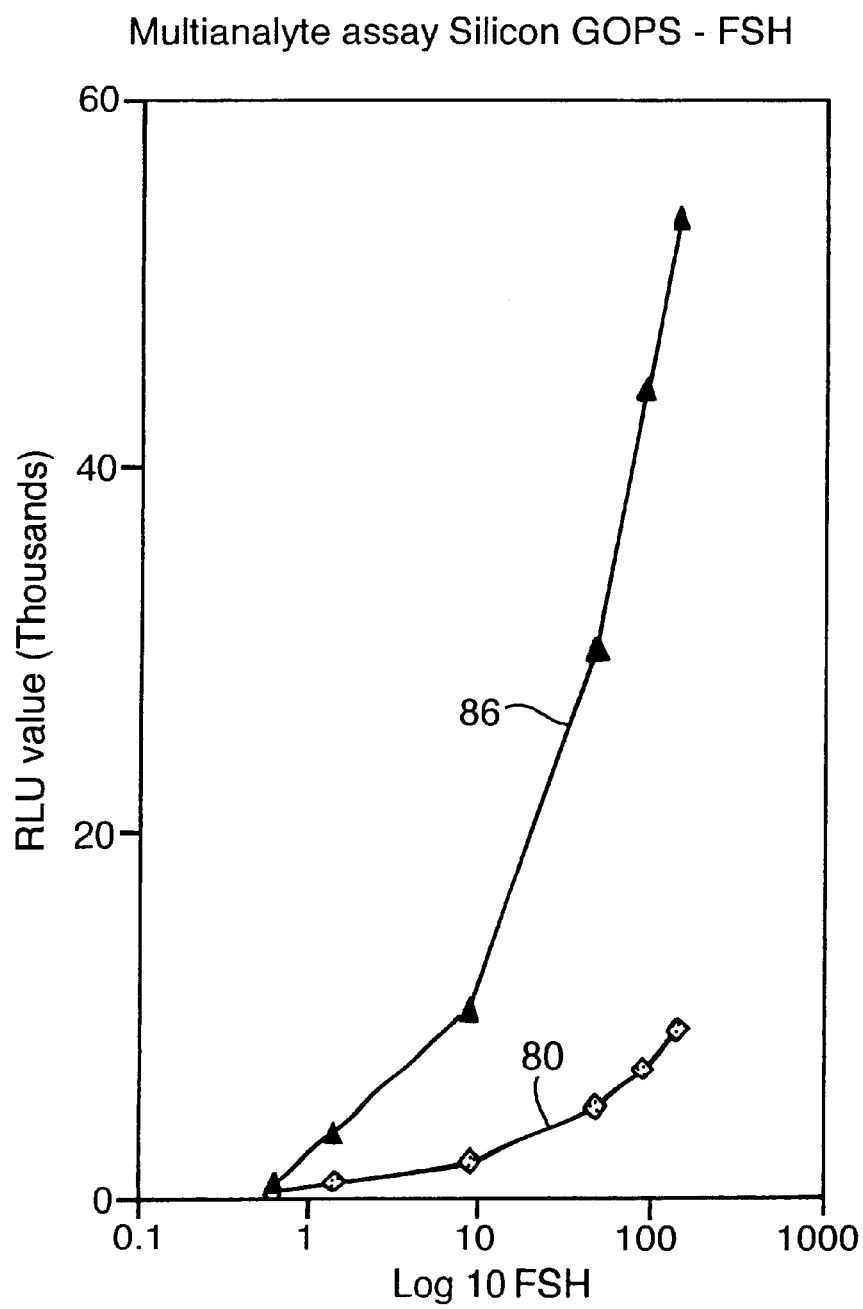
Figure 12:
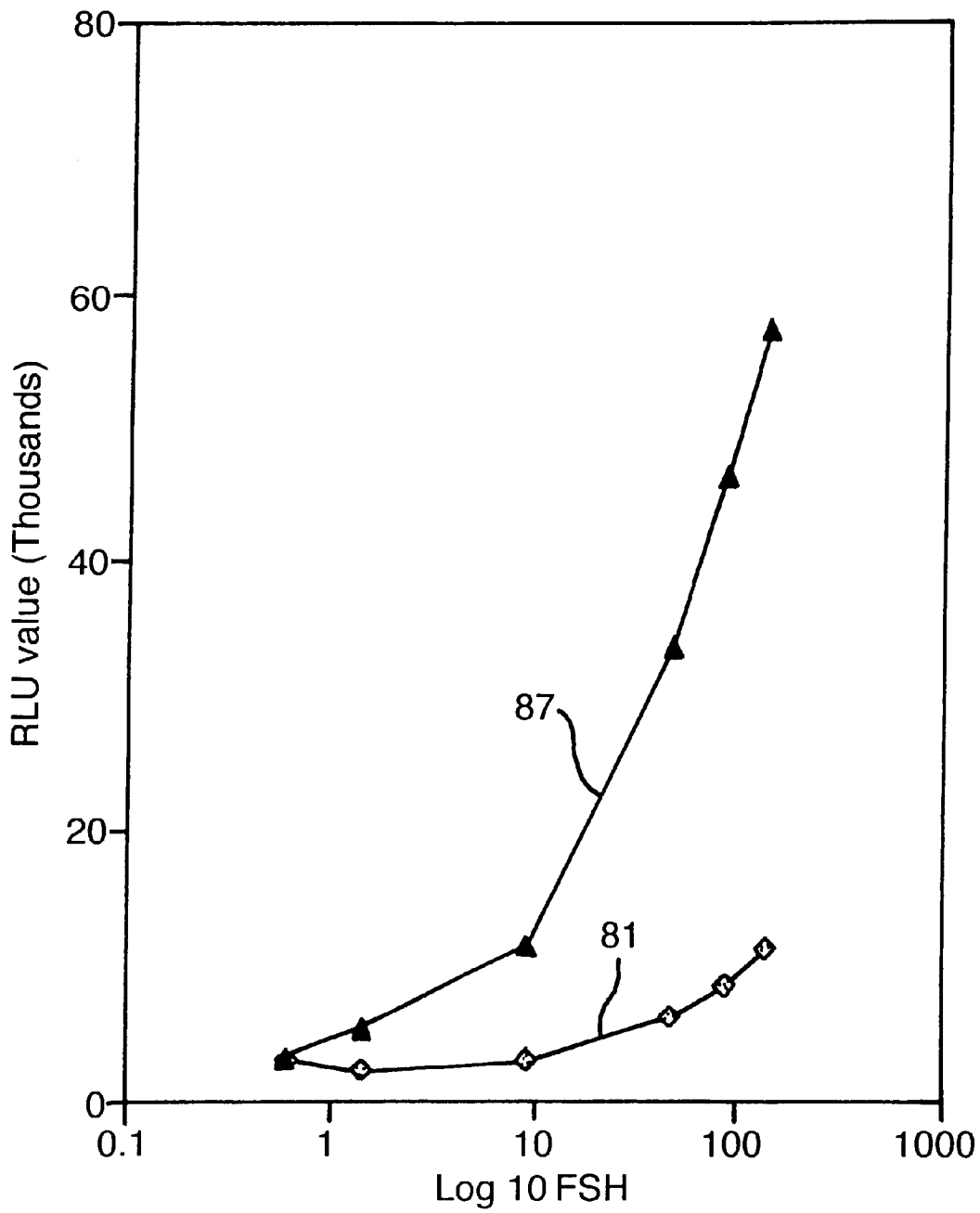

A method of performing an assay using the system of FIGS. 1 and 2 will now be described with reference to FIG. 6. In a first step 60, a substrate 2 is placed on the sample tray 1. The substrate 2 has a plurality of reaction sites, each bearing a ligand which reacts with a respective analyte A,B,C,D etc. At step 61, the sample tray 60 is moved by translation controls 3 until the substrate is located in dispensing position 11. At 62, the dispenser pump 10 dispenses a liquid test sample onto the substrate—for instance in the case of the substrate of FIG. 3 the test sample is dispensed into the reservoir 21. At 62', the dispenser pump 10 dispenses a liquid reagent onto the substrate. The liquid reagent comprises a mixture of labelled reagents A',B',C',D' etc which each react with a respective one of the analytes, i.e. A' reacts with A, B' reacts with B etc. The labelled reagents A',B',C',D' etc also all react with chemiluminescence reagent.

The test sample and labelled reagents then pass along the channels 21 into the reaction sites 23, exposing the various ligands to the test sample. The flow of liquid test sample and labelled reagents may be achieved by capillary attraction, centrifugal force, vacuum force or electroosmotic flow. The use of electroosmotic flow would avoid the need for valves, so that no moving mechanical parts are used. At 63 the substrate is washed to remove excess test sample which has not reacted at a reaction site 23.

At step 64 the dispenser pump 10 dispenses chemiluminescence reagent onto the substrate. This reacts with the labelled reagents A',B',C',D' etc in a chemiluminescent reaction. At 65, the translation controls 3 move the sample tray 1 until the substrates are in imaging position 9. At this stage, where an analyte has reacted with a ligand at one of the reaction sites, chemiluminescent radiation is being emitted from that reaction site by a respective labelled reagent. At 66, the CCD camera 6 with a suitable filter is exposed to generate an image of the chemiluminescent radiation emitted by the chip 2 in the imaging position 9, the image comprising an array of pixel values. The array of pixel values is input to the personal computer 7 via image output line 18, and stored in a memory (not shown) for analysis. At 67, the personal computer 7, under control of image processing software, analyses the image from the CCD camera 6 to generate a relative light unit (RLU) value for each reaction site. At 68, the personal computer 7 outputs the RLU values on a monitor or printer (not shown) and at 69 the personal computer 7 calculates a corresponding concentration for each analyte A,B,C,D etc in the test sample and outputs the calculated concentration on the printer or monitor.

The image processing algorithm 67 proceeds as follows:
a) The image is divided into a plurality of regions, each region containing one of the reaction sites and being defined by a two-dimensional array of pixels. The image is divided with reference to a previously stored map corresponding with the pattern of the reaction sites.
b) Within each region the computer 7 scans through and locates the most intense pixel. Let this intensity=X.
c) Next, it calculates 80% of this pixel intensity (=0.8X) and, hence, the top 20% range.
d) Finally, it identifies all pixels within that area of interest that fall within this range and averages the intensity of these pixels which it outputs as the top 20% signal intensity. Pixels that fall outside the range are discarded.

$$\text{TOP 20\% R L U signal} = \frac{\sum_{i=1}^{n} P_i}{n}$$

for all pixel intensities $P_i$, where $0.8X \leq P_i \leq X$

X=top signal, n=no. of pixels within the 80–100% range.

Other ranges can be used, 40% gives reasonably high intensities. Also, to remove any uncharacteristically high pixels, ranges of 80%→98% can be examined.

In an alternative method, in order to deal with abnormally high highest pixel values (which may result from bright spots caused by cosmic radiation), an additional step may be carried out between step a) and step b). In this additional step, each region is reviewed to determine whether there are any "rogue" values. For instance, with an array of one hundred pixel values, ninety-nine may lie between 0–100 RLUs and one "rogue" pixel may have a value of 2000 RLUs. The rogue pixel (or pixels) is discarded before step b). This step may be carried out manually, or by a suitable statistical algorithm.

If there is any inherent background in the image, this will be included in this signal. If all images are processed by this method, this will not necessarily be a problem but could be restrictive on the dynamic range. Therefore, mathematical morphology processing is used to remove background. Mathematical morphology is based on the use of set operators (intersection, union, inclusion, complement) to transform an image. The processed image has usually fewer details, implying a loss of information, but its main characteristics are still present. Once the image is simplified, quantitative analysis can be performed.

The principle of a basic operation transformation is based on the choice of a "structuring element", characterized by a shape, a size and the location of its centre. Each object of the image will be compared with this element and this is achieved by moving the element such that its centre hits all the points of the image. For each position of the element, one looks for the inclusion of the element with the objects of the image.

Figure 7:
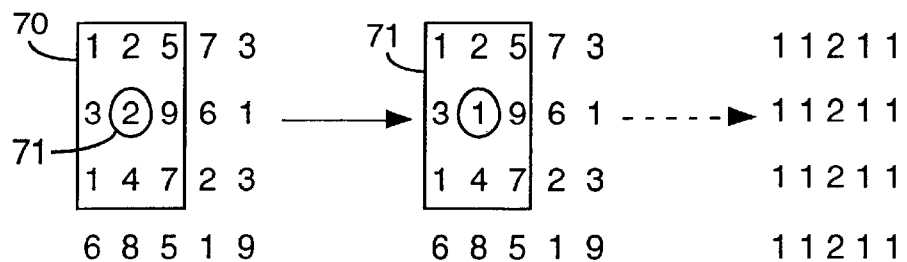
FIG. 7 illustrates erosion.

Erosion—removes isolated points and small particles, shrinks other particles, discards peaks on the boundary of the objects and disconnects some particles. In practice, with the structuring element, each central pixel is set to the lowest value in that particular position. Referring to FIG. 7, a pixel value in pixel location 70 at the centre of a 3×3 structuring element 71 is set to the lowest value within the structuring element 71, in this case value "1".

Figure 8:
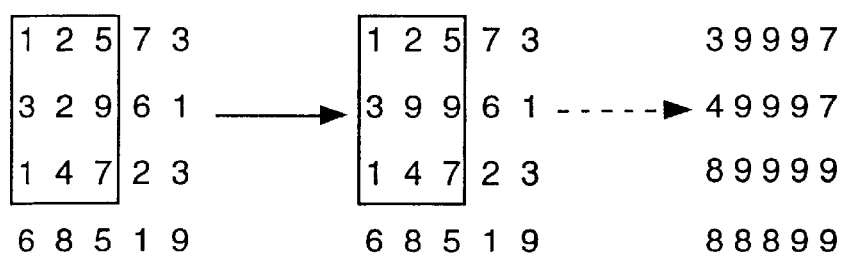
FIG. 8 illustrates dilation.

Dilation—fills small holes inside particles and gulfs on the boundary of objects, enlarges the size of the particles and may connect neighbouring particles. In practice, within the structuring element, each central pixel is set to the highest value in that particular position. This is illustrated in FIG. 8.

Opening—is a transformation which does not destroy as much information as erosion, and is the combination of an erosion followed by a dilation.

Opening gives an accurate determination of the background and can then be subtracted from the original image. Further use of thresholding then produces "clean" spots. One iteration is illustrate in FIG. 9. Increased iterations maintain high spot signal and give smoother edges.

Thresholding—sets the minimum intensity from which signal is read. This also helps to clean up the image and eliminate misleading background. Each spot is individually labelled and the intensity from the whole spot averaged.

The advantages of morphology are the removal of sloping background and the ability to distinguish between real signal and surrounding background. However, since the whole spot intensity is averaged, the actual signal tends to be very low.

A way around this problem is to use the morphology method, but instead of averaging the whole spot, average only the top 20% as outlined previously. This method results in high signals, but also an improved dynamic range due to the removal of background.

e.g. consider a top standard of 20,000 RLU and a bottom standard of 1200 RLU on a background of 600 RLU.

With background, $$\text{dynamic range} = \frac{20000}{1200} = 16.7$$

Without background, $$\text{dynamic range} = \frac{20000 - 600}{1200 - 600} = 32.3$$

Two illustrative methods of preparing substrates 2 and performing assays using the system of FIGS. 1 and 2 will now be described below.

EXAMPLE 1

Sulphonamide Multi-Analyte Assay

In this example 12 individual antibodies, each antibody specific for a single sulphonamide, were immobilised by covalent attachment by contact interactions on to discrete regions of a ceramic (aluminium oxide) substrate chemically modified epoxide surface.

The ceramic substances (1 cm×1 cm) were ultrasonically cleaned using an alkaline detergent (RBS35 @ 5% V/V) followed by double deionised water and then placed in 6M HCl for 16 hours. The chips (1 cm$^2$) were then placed in chromic acid for 1 hour in an ultrasonic bath.

The chips were washed exhaustively with double deionised water and acetone and then dried in an oven at 120° C. for 2 hours. Following this pretreatment, the chips were silanated using the organosilane γ-glycidoxypropyl trimethoxy silane (10% V/V) in anhydrous toluene, 4-dimethyl aminopyridine (1.25 g/L) and triethylamine (1% V/V). This mixture was refluxed for 4 hours and then left overnight at room temperature. The chips were washed with toluene and acetone before curing for 4 hours at 120° C.

Following the curing step the chips were placed in containers and stored at room temperature until required for spotting of sulphomanide antibodies. The sulphonamide antibodies were spotted using a BIODOT XY3000 dispenser in the pattern illustrated in FIG. 5. The sulphonamides assayed were sulphadoxine, sulphamethizole, sulphachlorophyridazine, sulphamethoxypyridazine, sulphamerazine, sulphapyridine, sulphisoxazole, sulphathiazole, sulphamethazine, sulphaquinoxaline, sulphadimethoxine, and sulphadiazine.

Dispense volumes of approx. 20 nl were employed for each sulphonamide antibody. The 12 sulphonamide antibodies which formed 12 discrete areas on the 1 cm$^2$ chip were incubated for 2 hours at 37° C. The chips were washed with phosphate buffered saline (pH7.2) containing 2% casein (W/V) and then blocked in same buffer overnight at +2–8° C. After washing with phosphate buffered saline (PBS) containing PEG300 (0.05% V/V) the chips were placed in the sample holder 1.

Multi-sulphonamide standards (200 μl) and a cocktail of sulphonamide horseradish peroxidase conjugates (100 μl) were added to the wells of the device as appropriate and incubated for 15 minutes at room temperature. The standards contained 5 ng/ml, 10 ng/ml, 50 ng/ml and 100 ng/ml for each of the 12 sulphonamides.

Figure 13:
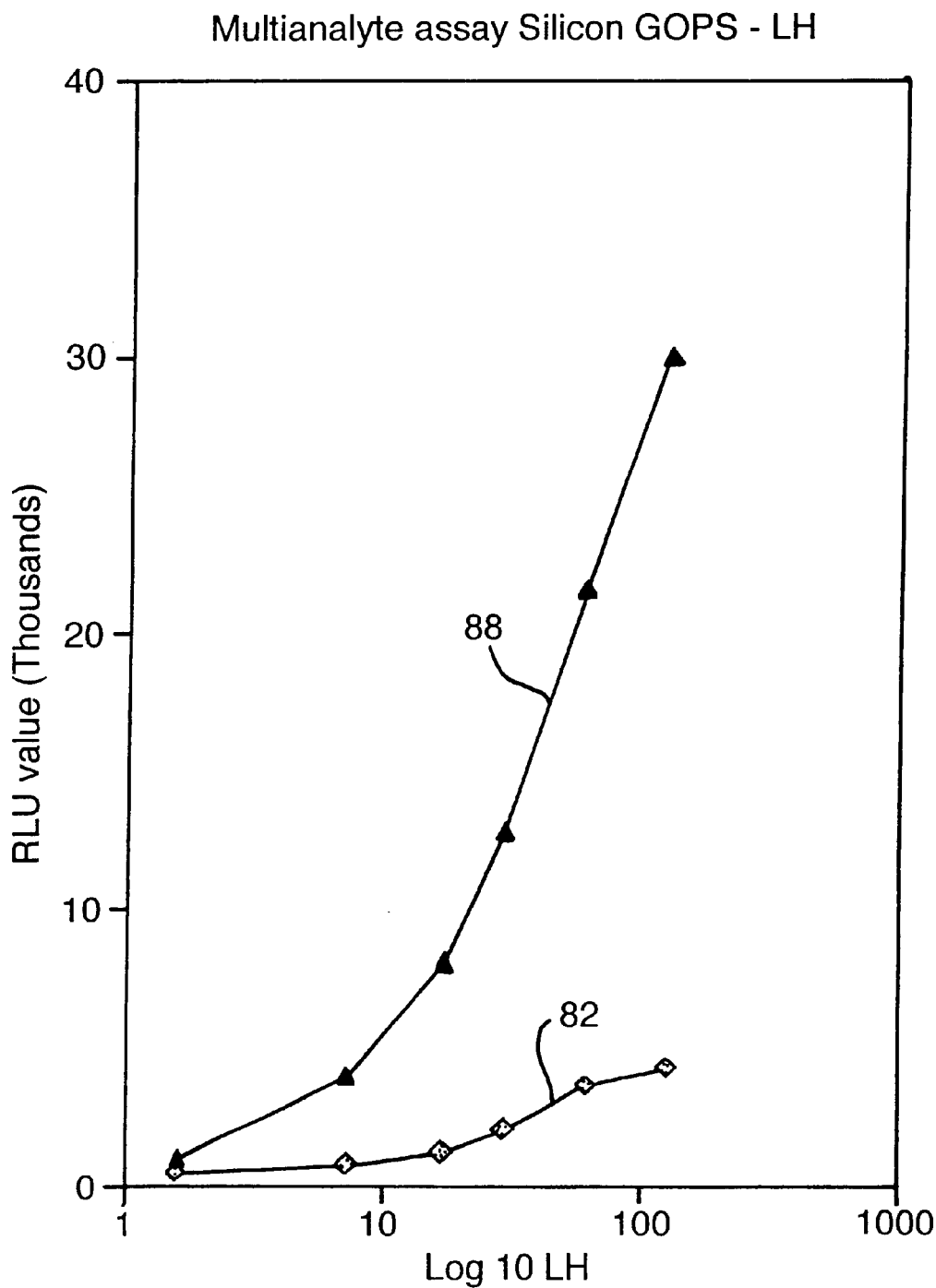
Figure 14:
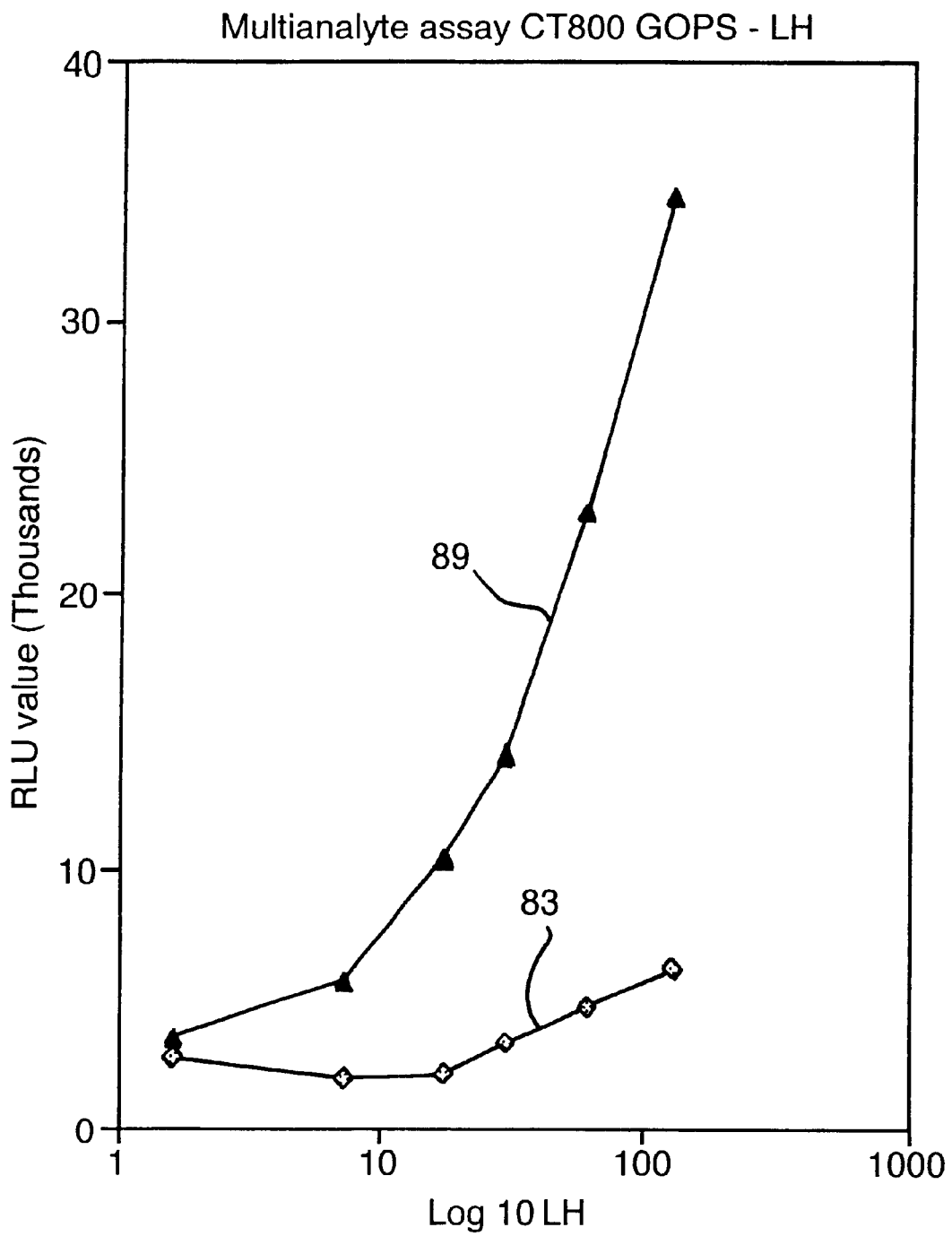
Figure 15:
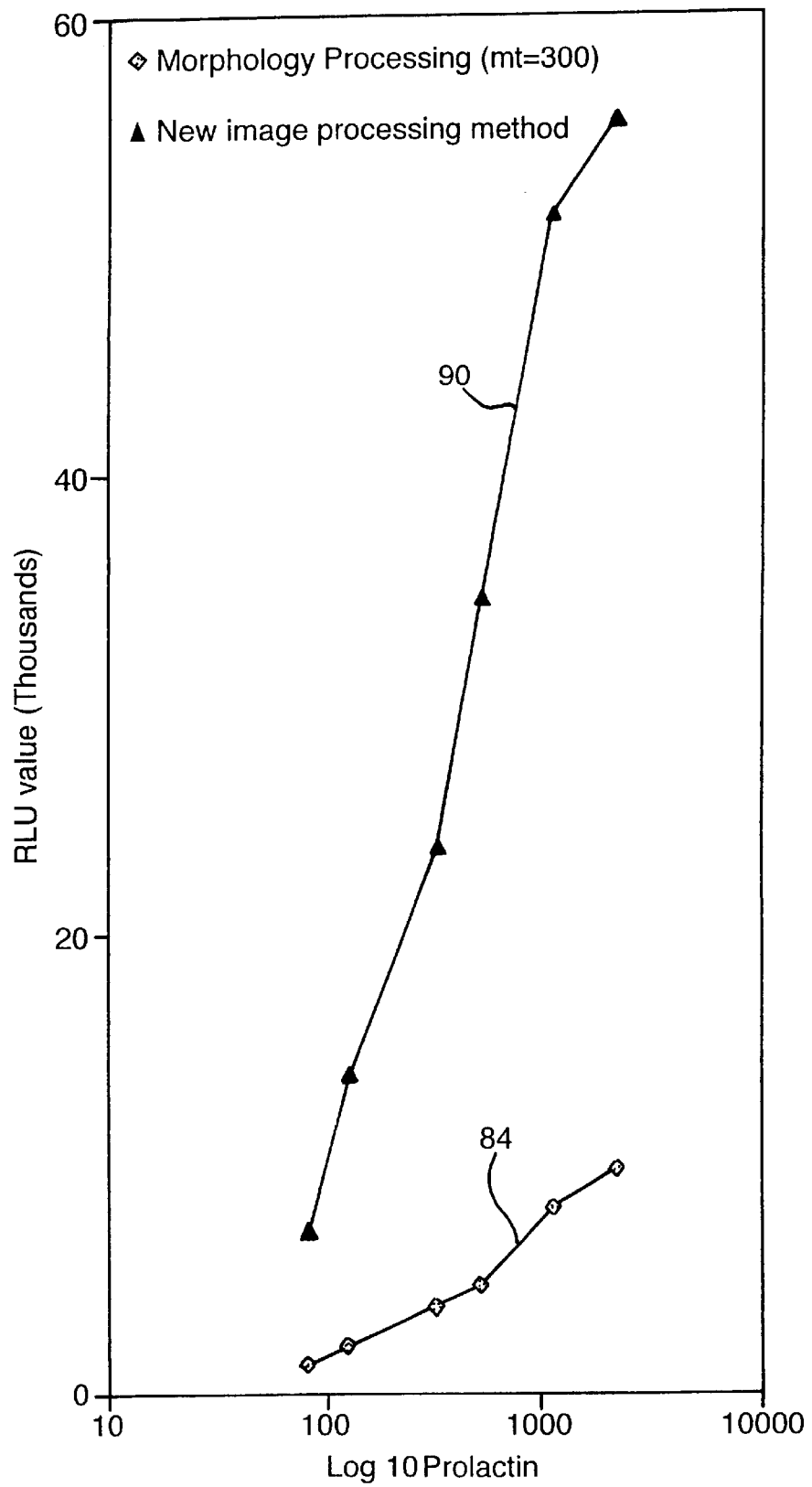

Thereafter the multi-sulphonamide chips were washed with PBS/PEG buffer to remove excess reagents and 300 μl chemiluminescent substrate [luminol(1.4 mM)/urea hydrogen peroxide (9.6 mM)] per chip was introduced. The chips were imaged using a CCD camera device with an exposure time of up to 4 minutes. A back-illuminated CCD camera is preferred, to improve the capture efficiency at the wavelength of the light generated by the chemiluminescent light reaction (approximately 433–445 nm in the case of luminol). The standard curves were obtained for each of the 12 individual sulphonamides using the new image-processing method. The calibration curves for each of the 12 individual sulphonamides are represented graphically in FIG. 13. The % B/Bo value plotted on the Y-axis represents the % inhibition of the zero standard RLU(Relative light unit) value caused by each individual sulphonamide standard (plotted on the X-axis as $\log_{10}$).

This example represents a multi-analyte assay for analytes of low molecular weight, where the assay is based on a competitive immunoassay format.

EXAMPLE 2

Multi-Analyte Assay for Prolactin (PL), Follicle Stimulating Hormone (FSH) and Luteinizing Hormone (LH)

In this example a multi-analyte assay was performed for 3 hormones of large molecular weight. This example represents a multi-analyte assay for a sandwich based immunoassay. No significant cross-reactivity were observed when the three hormones were determined in the same panel. The chemical pretreatment and silanation procedures were exactly as described in example 1.

The individual PL,FSH or LH monoclonal antibodies (approx.20 nl antibody dispensed) were immobilised on discrete areas of the chemically modified substrate. The multi-analyte assays were performed on both silicon and ceramic substrates with an epoxide surface as described in example 1.

In the assay 150 µl of a multiple LH/PL/FSH serum based standard and 150 µl of a diluent assay buffer were added to the chip and incubated for 15 minutes at room temperature. Following a wash step 300 µl of a single conjugate cocktail of LH-HRPO/PL-HRPO/FSH-HRPO conjugates was added and incubated for 15 minutes. Thereafter the chips were washed to remove excess reagents and the chemiluminescent reagent [luminol(1.4 mM)/urea hydrogen peroxide(9.6 mM)] was introduced.

The chips were imaged using a CCD camera device with an exposure time of up to 4 minutes. The standard curves for each of the hormones were plotted after the images were processed using both the traditional morphology/threshold method and the new image-processing method.

The standard curves are illustrated graphically in FIGS. 10–15. The standard curves obtained using the traditional morphology/threshold method are labelled 80–85. The standard curves obtained using an example of an image-processing method according to the present invention are labelled 86–91. It can be seen that the linearity and dynamic range indicated by the curves 86–91 is greater than the linearity and dynamic range indicated by the curves 80–85. The greater linearity and dynamic range offers a significant time saving to the end-user, since a wide dynamic range diminishes the need for the retesting of very high concentration test samples after additional dilution steps, to obtain an accurate result. The improved linearity/dynamic range also improves intra and inter-assay precision for test samples, since a small RLU change does not adversely affect results. The increased dynamic range has added benefits in terms of assay sensitivity, with improved discrimination of reaction site RLU values, enabling lower levels of analyte to be detected.

We claim:

1. A method of analyzing an image to obtain an image value, said image comprising a defined array of pixel values, said method comprising
    (1) determining a highest pixel value in said image;
    (2) calculating a lower threshold pixel value from said highest pixel value determined in said step (1) in accordance with a predetermined algorithm; and
    (3) obtaining said image value that represents a brightness of the image by statistically analyzing said pixel values in said image which lie in a range defined by said lower threshold pixel value calculated in said step (2).

2. A method according to claim 1, further comprising calculating an upper threshold pixel value from said highest pixel value determined in said step (1) in accordance with a second predetermined algorithm, wherein step (3) comprises statistically analysing pixel values in said image which lie in a range defined by said upper and said lower pixel threshold values.

3. A method according to claim 1, wherein said lower threshold pixel value is calculated as a predetermined percentage of said highest pixel value determined in said step (1).

4. A method according to claim 3, wherein said lower threshold pixel value is between 50% and 90% of said highest pixel value determined in said step (1).

5. A method according to claim 4, wherein said lower threshold pixel value is substantially 80% of said highest pixel value determined in said step (1).

6. A method according to claim 2, wherein said upper threshold pixel value is between 97% and 99% of said highest pixel value determined in said step (1).

7. A method according to claim 6, wherein said upper threshold pixel value is substantially 98% of said highest pixel value determined in said step (1).

8. A method according to claim 1, further comprising removing background from said pixel values.

9. A method according to claim 8, wherein said background is removed by a process selected from erosion, dilation, opening and thresholding.

10. A method of analyzing an image to obtain a plurality of image values, said image comprising an array of pixel values, said method comprising dividing said image into a plurality of regions, and obtaining an image value from each region by
    (1) determining a highest pixel value in said image region;
    (2) calculating a lower threshold pixel value from said highest pixel value determined in said step (1) in accordance with a predetermined algorithm; and
    (3) obtaining said image value that represents a brightness of the image by statistically analyzing said pixel values in said region which lie in a range defined by said lower threshold pixel value calculated in said step (2).

11. A method according to claim 1, further comprising detecting radiation from an original image to generate said array of pixel values.

12. A method according to claim 1, further comprising previously defining said defined array of pixel values by reviewing an original array of pixel values, and removing one or more of said highest pixel values in said original array of pixel values.

13. A method according to claim 1, wherein said image value is obtained in said step (3) by calculating the average of said pixel values.

14. A method according to claim 1, wherein said image has been obtained from a reaction site containing a reactive species which reacts with an analyte and which has been exposed to a test sample.

15. A method of analyzing a localized reaction site containing a reactive species which react with an analyte and which has been exposed to a test sample, the method comprising detecting radiation from said reaction site to generate an image comprising an array of pixel values, said radiation being indicative of the presence or absence of said analyte in said test sample; and analyzing said image by
    (1) determining a highest pixel value in said image;
    (2) calculating a lower threshold pixel value form said highest pixel value determined in said step (1) in accordance with a predetermined algorithm; and
    (3) obtaining said image value that represents a brightness of the image by statistically analyzing said pixel values in said image which lie in a range defined by said lower threshold pixel value calculated in said step (2), thereby obtaining an image value indicative of the presence or absence of the analyte in the test sample.

16. A method of analyzing a plurality of localized reaction sites, each containing a reactive species which reacts with a respective analyte and each having been exposed to a test sample, the method comprising detecting radiation from said reaction sites to generate an image comprising an array of pixel values, said radiation from each said reaction site being indicative of the presence or absence of a respective analyte in said test sample; dividing said image into a plurality of image regions each corresponding with a respective one of said reactions sites; and analyzing each image region by
    (1) determining a highest pixel value in said image region;
    (2) calculating a lower threshold pixel value from said highest pixel value determined in said step (1) in accordance with a predetermined algorithm; and
    (3) obtaining said image value that represent a brightness of the image by statistically analyzing pixel values in said image region which lie in a range defined by said lower threshold pixel value calculated in said step (2), thereby obtaining a plurality of image values each being indicative of the presence or absence of a respective analyte in the test sample.

17. A method according to claim 15, wherein said reaction site is located on a solid state substrate, and wherein said reactive species comprises a ligand covalently bonded to said substrate.

18. A method according to claim 17, wherein a surface of said substrate outside said reaction site is inert with respect to said analyte.

19. A method according to claim 15, wherein said radiation comprises one selected from chemiluminescent, bioluminescent and fluorescent radiation emitted from said reaction site.

20. A method of performing an assay, the method comprising exposing a reaction site to a test sample, said reaction site containing a reactive species which reacts with a respective analyte; and analyzing said reaction site by detecting radiation from said reaction site to generate an image comprising an array of pixel values, said radiation being indicative of the presence or absence of said analyte in said test sample; and analyzing said image by
  (1) determining a highest pixel value in said image;
  (2) calculating a lower threshold pixel value from said highest pixel value determined in said step (1) in accordance with a predetermined algorithm; and
  (3) obtaining said image value that represents a brightness of the image by statistically analyzing said pixel values in said image which lie in a range defined by said lower threshold pixel value calculated in said step (2), thereby obtaining an image value indicative of the presence or absence of the analyte in the test sample.

21. Apparatus for analyzing an image to obtain an image value, said image comprising a defined array of pixel values, said apparatus comprising
  (1) means for determining a highest pixel value in said image;
  (2) means for calculating a lower threshold pixel value from said highest pixel value in accordance with a predetermined algorithm; and
  (3) means for obtaining said image that represents a brightness of the image value by statistically analyzing pixel values in said image which lie in a range defined by said lower threshold pixel value.

22. Apparatus for analyzing a reaction site containing a reactive species which reacts with an analyte and which has been exposed to a test sample, said apparatus comprising means for detecting radiation from said reaction site to generate an image comprising an array of pixel values, said radiation from said reaction site being indicative of the presence or absence of a respective analyte in said test sample;
  (1) means for determining a highest pixel value in said image;
  (2) means for calculating a lower threshold pixel value from said highest pixel value in accordance with a predetermined algorithm; and
  (3) means for obtaining said image value that represents a brightness of the image by statistically analyzing pixel values in said image which lie in a range defined by said lower threshold pixel value, thereby obtaining one or more image values each being indicative of the presence or absence of a respective analyte in the test sample.

* * * * *